United States Patent
Byard et al.

(10) Patent No.: US 7,332,178 B2
(45) Date of Patent: Feb. 19, 2008

(54) STABLE NUTRITIONAL POWDER CONTAINING ASCORBYL PALMITATE

(75) Inventors: Julia A. Byard, Columbus, OH (US); Gary E. Katz, Columbus, OH (US); William T. Malone, Columbus, OH (US); David R. Wolf, Columbus, OH (US)

(73) Assignee: Abbott Laboratories, Abbott Park, IL (US)

( * ) Notice: Subject to any disclaimer, the term of this patent is extended or adjusted under 35 U.S.C. 154(b) by 533 days.

(21) Appl. No.: 10/423,172

(22) Filed: Apr. 25, 2003

(65) Prior Publication Data

US 2004/0213853 A1    Oct. 28, 2004

(51) Int. Cl.
| | |
|---|---|
| *A61K 47/00* | (2006.01) |
| *A61K 47/06* | (2006.01) |
| *A61K 47/16* | (2006.01) |
| *A61K 47/26* | (2006.01) |
| *A61K 47/42* | (2006.01) |
| *A61K 47/44* | (2006.01) |
| *A61K 9/14* | (2006.01) |

(52) U.S. Cl. ..................... 424/439; 424/489
(58) Field of Classification Search ............... 424/439, 424/479, 489, 499, 535, 810
See application file for complete search history.

(56) References Cited

U.S. PATENT DOCUMENTS

| | | | |
|---|---|---|---|
| 2,307,756 A | 1/1943 | Blaso | |
| 2,855,306 A | 10/1958 | Rosenberg | |
| 3,697,287 A * | 10/1972 | Winitz ........................ | 426/73 |
| 3,958,017 A * | 5/1976 | Morse et al. ................. | 426/72 |
| 3,998,753 A | 12/1976 | Antoshkiw | |
| 4,966,779 A | 10/1990 | Kirk | |
| 5,023,095 A | 6/1991 | Kirk | |
| 5,043,180 A | 8/1991 | Haring | |
| 5,077,069 A | 12/1991 | Chang | |
| 5,079,016 A | 1/1992 | Tood | |
| 5,084,289 A | 1/1992 | Shin | |
| 5,141,758 A * | 8/1992 | Monte ......................... | 426/72 |
| 5,153,012 A | 10/1992 | Ohtaka | |
| 5,234,702 A | 8/1993 | Katz | |
| 5,518,751 A | 5/1996 | de Boer | |
| 5,550,146 A | 8/1996 | Acosta | |
| 5,626,883 A * | 5/1997 | Paul ........................... | 424/605 |
| 6,071,963 A | 6/2000 | Tritsch | |
| 6,093,348 A | 7/2000 | Kowalski | |
| 6,475,539 B1 * | 11/2002 | DeWille et al. ............... | 426/72 |
| 2001/0022980 A1 * | 9/2001 | Bell et al. ................... | 424/771 |
| 2002/0127303 A1 * | 9/2002 | Chen et al. ................... | 426/89 |
| 2004/0001817 A1 * | 1/2004 | Giampapa .................. | 424/94.1 |
| 2004/0047896 A1 * | 3/2004 | Malnoe et al. .............. | 424/439 |

FOREIGN PATENT DOCUMENTS

EP        0198804        10/1986

OTHER PUBLICATIONS

Oxford Pocket American Dictionary of Current English; Oxford University Press: New York, 2002, p. 312.*
Brown, T. L. et al. Chemistry: The Central Science, 6th edn.; Prentice Hall: Englewood Cliffs, NJ, 1994; p. 142.*
Abstract: WO20057876 Antioxidant formulation, useful for inhibiting oxidative stress and associated disease, containing tocotrienol and radical scavenger recycler, Oct. 5, 2000.
Publication: Dougherty, The Effectiveness of Natural Antioxidants Compared to Synthetic Antioxidants, 1993.

* cited by examiner

*Primary Examiner*—Johann R. Richter
*Assistant Examiner*—James H Alstrum-Acevedo
(74) *Attorney, Agent, or Firm*—William J. Winter; Sandra E. Weida

(57) ABSTRACT

Disclosed are nutritional powders, including lactose-free powders or other oxidatively sensitive nutritional powders, comprising at least about 400 ppm by weight of ascorbyl palmitate, preferably in combination with at least about 300 ppm by weight of cystine, cysteine, or combinations thereof. It has been found that these powders, especially the lactose-free embodiments, have improved stability as measured by sensory performance and reduced vitamin A degradation during prolonged storage.

10 Claims, No Drawings

STABLE NUTRITIONAL POWDER CONTAINING ASCORBYL PALMITATE

TECHNICAL FIELD

The present invention relates to nutritional powders, especially lactose-free formulas, comprising selectively high ascorbyl palmitate concentrations for improved sensory performance and Vitamin A stability.

BACKGROUND OF THE INVENTION

Nutritional powders are well known for use in providing various individuals with sole or supplemental nutritional. These powders are reconstituted with water or other aqueous liquid by the ultimate user to form a nutritional liquid or beverage. These powders most often contain varying amounts and types of protein, carbohydrate, lipid, vitamins and minerals, all depending largely upon the nutritional needs of the intended user.

Nutritional powders often contain a variety of lipids, including unsaturated lipids that tend to be more oxidatively sensitive than some other ingredients. This is especially significant in the formulation of infant nutritional powders since infant formulas typically contain a variety of oxidatively sensitive materials such as unsaturated fatty acids. These fatty acids require additional care during processing to ensure that the unsaturated fatty acids (e.g., linolenic acid, linoleic acid, docosahexaenoic acid, arachidonic acid.) in the finished powder do not excessively degrade by way of oxidation during prolonged storage periods of up to about 36 months, typically from about 24 to about 36 months.

A variety of methods have been used to control oxidative processes in nutritional powders during prolonged storage. Many such methods, of course, are directed to the control of formulation, processing, and packaging conditions that ultimately lead to a more oxidatively stable packaged product. Other methods include the use of a variety of known antioxidants or other stability-promoting ingredients such as ascorbyl palmitate, tocopherols, beta carotene, and even some synthetic materials such as hydroxy anisole (BHA) and butylated hydroxy toluene (BHT) where appropriate.

One such method of providing a more stable nutritional powder is described in U.S. Pat. No. 5,234,702 (Katz et al.) in which a nutritional powder with an oil blend of soy and marine oils is formulated with an antioxidant system made up of ascorbyl palmitate, beta carotene and/or mixed tocopherols, and citrate. This particular method is especially useful in minimizing the undesirable rancidity that often results when unsaturated oils and fatty acids are exposed to the heat and air commonly associated with spray drying processes. The Katz et al. reference teaches that the combination of ingredients provides a highly effective means for improving product stability, even though individual ingredients such as ascorbyl palmitate by themselves were not particularly effective.

It has now been found that lactose-free nutritional powders, including lactose-free infant formulas, are especially susceptible to oxidative processes during prolonged storage, and thus can be more sensitive to vitamin A degradation and the development of rancid oils. Compared to other nutritional powders, these lactose-free powders are often more susceptible to undesirable oxidative processes, and thus represent a sizable challenge for the formulator to produce a stable finished product that will not develop a rancid character during prolonged storage.

It has also been found that these lactose-free nutritional powders, as well as most any nutritional powder containing unsaturated fatty acids and similar other materials, can be formulated into a stable, packaged powder provided that it is formulated with ascorbyl palmitate at a selectively high concentration of at least about 400 ppm, typically from about 400 to about 1000 ppm by weight of the powder. Although ascorbyl palmitate is a known antioxidant for use in various oils, it is also generally known that it is not highly effective when used alone in a nutritional powder.

It has also been found that nutritional powders, especially lactose-free nutritional powders and other oxidatively unstable powders, can also be further stabilized for prolonged storage by the combined use of ascorbyl palmitate at selectively high concentrations as described herein, with at least about 300 ppm of cystine and/or cysteine, by weight of the powder.

SUMMARY OF THE INVENTION

The present invention is directed to nutritional powders, especially lactose-free nutritional powders or powders containing unsaturated lipids, comprising by weight of the powder, at least about 400 ppm of ascorbyl palmitate, or a combination of the ascorbyl palmitate with at least about 300 ppm of cystine and/or cysteine.

It has been found that these compositions remain oxidatively more stable over prolonged periods as evidenced by reduced Vitamin A degradation and improved sensory scores suggestive of reduced oil oxidation. It has also been found that these compositions are especially useful when used in the context of lactose-free nutritional formulas, which it has also been found are especially susceptible to oxidative processes that lead to sensory development of rancid oils. It has been found that this stability can be achieved without reliance upon complex antioxidation systems, and instead relies upon the use of selectively high ascorbyl palmitate concentrations, alone or in combination with at least about 300 ppm by weight of cystine and/or cysteine.

DETAILED DESCRIPTION OF THE INVENTION

The nutritional powders of the present invention, including lactose-free nutritional powders and other oxidatively sensitive nutritional powders, comprise select concentrations of ascorbyl palmitate, preferably in combination with cystine and/or cysteine. These and other essential elements or limitations of the nutritional powders and methods of the present invention are described in detail hereinafter.

The term "nutritional powder" as used herein, unless otherwise specified, refers to flowable or substantially flowable particulate compositions, or at least particulate compositions that can be easily scooped with a spoon, wherein the compositions are reconstituted with a suitable fluid, typically water, to form a liquid nutritional composition for use in the desired targeted group, e.g., adults, pediatrics including infants and toddlers, diabetics, critical care patients, or non-humans such as livestock, pets, and wildlife. These "nutritional powders" are preferably formulated to provide the sole or primary nutritional needs of the intended user, although it is understood that these powders can also be formulated to provide, or otherwise be used as, a secondary or minor nutritional supplement providing one or more of protein, carbohydrate, lipid, vitamins and minerals.

The term "lipid" as used herein, unless otherwise specified, means fats, oils, and combinations thereof.

The term "infant" as used herein refers to children not more than one year of age, and includes infants from 0 to about 4 months of age, infants from about 4 to about 8 months of age, infants from about 8 to about 12 months of age, low birth weight infants at less than 2,500 grams at birth, and premature infants born at less than about 37 weeks gestational age, typically from about 26 weeks to about 34 weeks gestational age.

The term "infant formula" as used herein refers to a nutritional composition designed for infants, which preferably contains sufficient protein, carbohydrate, lipid, vitamins, minerals, and electrolytes to potentially serve as the sole source of nutrition when provided in sufficient quantity.

All percentages, parts and ratios as used herein are by weight of the total composition, unless otherwise specified. All such weights as they pertain to listed ingredients are based on the active level and, therefore, do not include solvents or by-products that may be included in commercially available materials, unless otherwise specified.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, 5, 6, from 1 to 9, from 3.6 to 4.6, from 3.5 to 9.9, and so forth.

All references to singular characteristics or limitations of the present invention shall include the corresponding plural characteristic or limitation, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The nutritional powders of the present invention can comprise, consist of, or consist essentially of the essential elements and limitations of the invention described herein, as well as any additional or optional ingredients, components, or limitations described herein or otherwise useful in nutritional powder applications.

Ascorbyl Palmitate

The nutritional powders of the present invention comprise selectively high concentrations of ascorbyl palmitate, alone or in combination with cystine and/or cysteine, to provide a surprisingly stable nutritional powder system. These materials are described in detail hereinafter.

The ascorbyl palmitate concentrations in the nutritional powders of the present invention must be at least about 400 ppm, preferably from about 400 ppm to about 1,000 ppm, more preferably from about 500 to about 900, most preferably from about 600 to about 800 ppm, by weight of the nutritional powder.

Ascorbyl palmitate is a known anti-oxidant suitable for use in a variety of food and nutritional products, including nutritional powders. It is generally known, however, that ascorbyl palmitate is often insufficient by itself in providing the desired level of anti-oxidant activity, especially in an otherwise highly oxidatively sensitive matrix such as one containing high concentrations of unsaturated lipids and oils, or in lactose-free formulas as described herein.

It has now been found that ascorbyl palmitate can be highly effective in an oxidatively sensitive powder containing unsaturated lipids and oils, even when used alone or in combination with few other anti-oxidants, provided that the ascorbyl palmitate concentrations are selected from within the relatively high concentration ranges described herein. It has also been found that oxidatively unstable powders such as lactose-free nutritional powders are especially susceptible to oxidation and the development of a rancid oil character, and that the use of selectively high concentrations of ascorbyl palmitate in these powders can provide highly effective anti-oxidative stability without the need to formulate with additional combinations of anti-oxidants.

Ascorbyl palmitate is available from a variety of suppliers and manufacturers, including Ascorbyl Palmitate NF, FCC, available from Hoffman-LaRoche, Inc.

Cystine

The nutritional powders of the present invention may further comprise cystine, cysteine, or combinations thereof. To be effective, the cystine and/or cysteine must be used in combination with the ascorbyl palmitate component hereof, and must be used at a concentration of at least about 300 ppm, preferably from about 300 ppm to about 2,500 ppm, more preferably from about 800 ppm to about 2,000 ppm, even more preferably from about 800 ppm to about 1,200 ppm by weight of the nutritional powder.

Both cystine and cysteine, individually or in combination, can be used in the nutritional powder of the present invention to provide enhanced oxidative stability. Cystine is a nonessential amino acid commonly derived from the hydrolysis of protein, whereas cysteine is a nonessential amino acid derived from cystine itself. Both of these materials are commonly used in food and other nutritional products as nutrient and dietary supplements.

It has now been found that cystine and/or cysteine can be used in combination with ascorbyl palmitate to provide enhanced oxidative stability, and are especially useful when formulated into oxidatively unstable systems containing unsaturated lipids and oils or the lactose-free nutritional powders as described herein. Many of a variety of known or otherwise suitable sources of cystine and/or cysteine can be used in the formulation, for example L-cysteine dihydrochloride, L-cystine dihydrochloride, and combinations thereof.

Nutrients

The nutritional powders of the present invention comprise sufficient types and amounts of nutrients to meet the targeted needs of the intended user. These powders may comprise one or more of lipid, protein, or carbohydrate, and preferably also contain one or more of vitamins and minerals.

Many different sources and types of carbohydrates, lipids, proteins, minerals and vitamins are known and can be used in the nutritional powders of the present invention, provided that such nutrients are compatible with the added ingredients in the selected powder composition, are safe and effective for their intended use, and do not otherwise unduly impair product performance.

Carbohydrates suitable for use in the nutritional powders of the present invention can be simple or complex, lactose-containing or lactose-free, or combinations thereof. Non-limiting examples of suitable carbohydrates include hydrolyzed corn starch, maltodextrin, glucose polymers, sucrose, corn syrup, corn syrup solids, rice-derived carbohydrate, glucose, fructose, lactose, high fructose corn syrup and indigestible oligosaccharides such as fructooligosaccharides (FOS), and combinations thereof.

Proteins suitable for use in the nutritional powders of the present invention can be hydrolyzed, partially hydrolyzed or non-hydrolyzed, and can be derived from any known or otherwise suitable source such as milk (e.g., casein, whey), animal (e.g., meat, fish), cereal (e.g., rice, corn), vegetable (e.g., soy), or combinations thereof. The proteins for use herein can include, or be entirely or partially replaced by, free amino acids known for use in nutritional products, non-limiting examples of which include tryptophan, glutamine, tyrosine, methionine, cysteine, arginine, and combinations thereof.

Lipids suitable for use in the nutritional powders include, but are not limited to, coconut oil, soy oil, corn oil, olive oil, safflower oil, high oleic safflower oil, MCT oil (medium chain triglycerides), sunflower oil, high oleic sunflower oil, palm and palm kernel oils, palm olein, canola oil, marine oils, cottonseed oils, and combinations thereof.

Other suitable lipids or related materials include those that provide specific fatty acids, including arachidonic acid, docosahexaenoic acid, and mixtures thereof. These materials are known to provide beneficial effects in infants such as enhanced brain and vision development, descriptions of which are set forth in U.S. Pat. No. 5,492,938 to Kyle et al., which descriptions are incorporated herein by reference. Non-limiting sources of arachidonic acid and docosahexaenoic acid include marine oil, egg derived oils, fungal oil, algal oil, and combinations thereof.

The nutritional powders may further comprise any of a variety of vitamins, non-limiting examples of which include vitamin A, vitamin D, vitamin E, vitamin K, thiamine, riboflavin, pyridoxine, vitamin $B_{12}$, niacin, folic acid, pantothenic acid, biotin, vitamin C, choline, inositol, salts and derivatives thereof, and combinations thereof.

The nutritional powders may further comprise any of a variety of minerals, non-limiting examples of which include calcium, phosphorus, magnesium, iron, zinc, manganese, copper, iodine, sodium, potassium, chloride, and combinations thereof.

Lactose-Free Embodiments

The nutritional powders of the present invention include lactose-free embodiments, which includes both low-lactose formulas as well as compositions containing little or no measurable lactose. Any lactose-free carbohydrate known for use in nutritional powders, or otherwise effective for such use, can be used as a carbohydrate component in the lactose-free embodiments of the present invention.

The lactose-free embodiments of the present invention include low-lactose formulations having less than 50%, preferably less than 25%, more preferably less than 1%, lactose as a percentage of the total carbohydrate calories in the formula. These lactose-free embodiments most preferably contain little or no measurable lactose, wherein the formula contains no more than about 200 ppm, or about 30 mg of lactose per 100 kcal of formula as determined by High Performance Liquid Chromatography in accordance with the method described in U.S. Ser. No. 10/193,516, filed Jul. 11, 2002, which description is hereby incorporated herein by reference.

Non-limiting examples of suitable lactose-free carbohydrates include hydrolyzed or intact, naturally or chemically modified, starches sourced from corn, tapioca, rice or potato, in waxy or non-waxy forms. Other non-limiting examples of suitable carbohydrates include hydrolyzed cornstarch, maltodextrin, glucose polymers, sucrose, corn syrup, corn syrup solids, glucose, fructose, high fructose corn syrup, indigestible oligosaccharides, such as fructooligosaccharides (FOS), and combinations thereof.

It has also been found that lactose-free nutritional powders, including lactose-free infant formulas, are especially susceptible to oxidative processes during prolonged storage. Compared to other nutritional powders, these lactose-free powders are often more susceptible to undesirable oxidative processes, and thus represent a sizable challenge for the formulator to produce a stable finished product that will not develop an excessively rancid character during prolonged storage.

It has also been found that these lactose-free nutritional powders can be formulated into a stable, packaged powder provided that it is formulated with ascorbyl palmitate at the selectively high concentrations defined herein. It has also been found that these lactose-free nutritional powders can also be further stabilized for prolonged storage by the combined use of the selectively high ascorbyl palmitate concentrations in combination with at least about 300 ppm of cystine and/or cysteine.

Infant Formula Embodiments

The infant formula embodiments of the present invention preferably comprise nutrients in accordance with the relevant infant formula guidelines for the targeted consumer or user population, an example of which would be the Infant Formula Act, 21 U.S.C. Section 350(a).

The infant formulas preferably contain one or more of protein, lipid, and carbohydrate nutrients, and will most typically comprise all three. Preferred carbohydrate, lipid, and protein concentrations for use in the infant formulas are set forth in the Table 1.

TABLE 1

Infant Formula Nutrients*

| Nutrient | Range | gram/ 100 kcal | Gram/ 100 gram powder | Gram/liter (reconstituted) |
|---|---|---|---|---|
| Carbohydrate | Preferred | 8-16 | 30-90 | 54-108 |
|  | More preferred | 9-13 | 45-60 | 61-88 |
| Lipid | Preferred | 3-8 | 15-35 | 20-54 |
|  | More preferred | 4-6.6 | 20-30 | 27-45 |
| Protein | Preferred | 1-3.5 | 8-17 | 7-24 |
|  | More preferred | 1.5-3.4 | 10-17 | 10-23 |

*all numerical values preceded by the term "about"

The infant formula embodiments also preferably include per 100 kcal of formula one or more of the following: vitamin A (from about 250 to about 750 IU), vitamin D (from about 40 to about 100 IU), vitamin K (greater than about 4 µm), vitamin E (at least about 0.3 IU), vitamin C (at least about 8 mg), thiamine (at least about 8 µg), vitamin $B_{12}$ (at least about 0.15 µg), niacin (at least about 250 µg), folic acid (at least about 4 µg), pantothenic acid (at least about 300 µg), biotin (at least about 1.5 µg), choline (at least about 7 mg), and inositol (at least about 4 mg).

The infant formula embodiments also preferably include per 100 kcal of formula one or more of the following: calcium (at least about 50 mg), phosphorus (at least about 25 mg), magnesium (at least about 6 mg), iron (at least about 0.15 mg), iodine (at least about 5 µg), zinc (at least about 0.5 mg), copper (at least about 60 µg), manganese (at least about 5 µg), sodium (from about 20 to about 60 mg), potassium (from about 80 to about 200 mg), and chloride (from about 55 to about 150 mg).

The infant formula embodiments preferably comprise lipid materials such as arachidonic acid and docosahexaenoic acid, which have been shown to have beneficial effects in infants, including enhanced brain and vision development. These lipids and some of their effects are described, for example, in U.S. Pat. No. 5,492,938 (Kyle et al.), which description is incorporated herein by reference. Sources of these lipids include, but are not limited to, marine oil, egg derived oils, fungal oil, algal oil, and combinations thereof.

The infant formula embodiments of the present invention preferably comprise a combination of arachidonic acid and docosahexaenoic acid, alone or in further combination with linoleic acid and linolenic acid. Arachidonic acid concentrations preferably range up to about 1.0%, more preferably from about 0.2% to about 1.0%, even more preferably from about 0.35% to about 0.7%, and most preferably from about 0.4% to about 0.5%, by weight of the total fatty acids in the formula. Docosahexaenoic acid concentrations preferably range up to about 1.0%, more preferably from about 0.15% to about 1.0%, and even more preferably from about 0.19% to about 0.36%, by weight of the total fatty acids in the formula. Linoleic concentrations preferably range up to about 30%, more preferably from about 10% to about 30%, and even more preferably from about 15% to about 20%, by weight of the total fatty acids in the formula. Linolenic acid concentrations preferably range up to about 4%, more preferably from about 1.5% to about 4%, even more preferably from about 2% to about 3%, and even more preferably from about 2.2% to about 2.6%. These preferred lipid materials are described in U.S. Pat. No. 6,495,599 (Auestad et al.), which description is incorporated herein by reference.

Method of Use

The present invention is also directed to a method of providing an individual with their sole, primary, or supplemental nutrition needs. The method preferably comprises reconstituting the powder with an aqueous vehicle, most typically water, to form the desired nutritional beverage or liquid, which is then orally or enterally consumed to provide the individual with the desired nutrition. The reconstituted powders can be formulated for use in a variety of specific populations such as adults, pediatrics including infants and toddlers, diabetics, critical care patients, or other human populations with specific or unique nutritional needs.

For infant formula embodiments of the present invention, the nutritional powder is reconstituted to the desired caloric density or other suitable measure of dilution. The most commonly used caloric density for infant formulas are at least about 19 kcal/fl oz (660 kcal/liter), more typically from about 20 kcal/fl oz (675-680 kcal/liter) to about 25 kcal/fl oz (820 kcal/liter), even more typically from about 20 kcal/fl oz (675-680 kcal/liter) to about 24 kcal/fl oz (800-810 kcal/liter). Generally, the 22-24 kcal/fl oz formulas are used in pre-term of low birth weight infants, and the 20-21 kcal/fl oz (675-680 to 700 kcal/liter) formulas are more often used in term infants. The quantity of a nutritional infant powder required to produce a volume suitable for one infant feeding can vary, but generally ranges from about 8 to about 9 grams of nutritional powder reconstituted with about 55 to about 65 ml of water to produce the desired nutrient densities.

The methods of the present invention are therefore directed to the reconstitution of the nutritional powders of the present invention with a suitable aqueous liquid, preferably water, followed by oral or enteral administration of the resulting nutritional liquid to provide the individual, including infants, with their sole, primary, or supplemental nutrition.

Optional Ingredients

The nutritional powders of the present invention may further comprise other optional components that may modify the physical, chemical, aesthetic or processing characteristics of the compositions or serve as pharmaceutical or additional nutritional components when used in the targeted population. Many such optional ingredients are known for use in food and nutritional products, including powder infant formulas, and may also be used in the nutritional powders of the present invention, provided that such optional materials are compatible with the essential materials described herein, are safe and effective for their intended use, and do not otherwise unduly impair product performance.

Non-limiting examples of such optional ingredients include preservatives, additional anti-oxidants, emulsifying agents, buffers, colorants, flavors, vitamins, minerals, nucleotides and nucleosides, thickening agents and stabilizers, and so forth.

Product Form

The nutritional powders of the present invention are typically in the form of flowable or substantially flowable particulate compositions, or at least particulate compositions that can be easily scooped and measured with a spoon or similar other device, wherein the compositions can easily be reconstituted by the intended user with a suitable aqueous fluid, typically water, to form a liquid nutritional composition for immediate oral or enteral use in the desired group. In this context, "immediate" use means within about 48 hours, preferably within about 24 hours, more preferably right after, reconstitution.

The nutritional powders include spray dried, dry mixed or other known or otherwise effective particulate form, and are easily distinguished visually from liquid nutritional products or non-flowable product forms such as nutritional bars. Each can be packaged and sealed in a single or multi-use container and stored under ambient conditions for up to about 24 months, more typically from about 12 to about 18 months. For multi-use containers, these packages can be opened and then covered for repeated use by the ultimate user, provided that the covered package is then stored under ambient conditions (e.g., avoid extreme temperatures) and the contents used within about one month.

Method of Manufacture

The nutritional infant formulas of the present invention may be prepared by any known or otherwise effective technique suitable for making and formulating nutritional powders. Many such methods are described in the nutritional art or are otherwise well known to those skilled in the nutritional art.

Nutritional powders are often prepared by simply forming a slurry from one or more aqueous solutions or mixtures containing carbohydrates, proteins, lipids, stabilizers or other processing aids, vitamins, and minerals, followed by emulsification and homogenization of the resulting liquid, which is then cooled. The resulting emulsion is then heated and dried into powder form, which might be accomplished by spray drying or other heat-treating methods of forming solid particulates in a powder matrix. Other essential or optional materials can also be added to the formulation by dry blending, agglomerating, or otherwise combining the added material to the forming or just formed solid particulates.

Methods of making nutritional powders are described, for example, in U.S. Pat. No. 6,365,218 (Borschel), which description is incorporated herein by reference.

EXAMPLES

The following examples further describe and demonstrate specific embodiments within the scope of the present invention. The examples are given solely for the purpose of illustration and are not to be construed as limitations of the present invention, as many variations thereof are possible without departing from the spirit and scope of the invention. All exemplified amounts are weight percentages based upon the total weight of the composition, unless otherwise specified.

Example 1

This example illustrates an infant nutritional powder of the present invention, including a method of using and making the formula. The formula ingredients for a 3,400 kg batch are listed below in Table 1.1.

TABLE 1.1

Infant Formula Powder

| INGREDIENT | AMOUNT |
| --- | --- |
| High oleic sunflower, coconut, and soy oil | 995 kg |
| Ascorbyl palmitate | 2.9 kg |
| Oil soluble vitamin premix | 1.5 kg |
| Milk protein isolate | 414 kg |
| Calcium phosphate | 44 kg |
| Calcium carbonate | 0.54 kg |
| Potassium citrate | 37 kg |
| Magnesium chloride | 3.9 kg |
| Potassium chloride | 7.9 kg |
| Lactose | 481 kg |
| Maltodextrin | 481 kg |
| Corn Syrup | 1,202 kg |
| Ferrous sulfate | 0.154 kg |
| Vitamin/trace mineral/free amino acid premix | 5 kg |
| Choline chloride | 1.5 kg |
| Ascorbic acid | 5.4 kg |

To prepare the nutritional powder, an aqueous slurry containing the formula carbohydrates and minerals is formed with heat and agitation. An oil blend is then prepared which contains the formula oils, antioxidants and oil soluble vitamins. The protein is then added to the oil blend followed by the addition of the aqueous slurry, all with agitation. The pH of the resulting combination is adjusted as needed to reach 6.5-6.9. The combination is then heat-treated and homogenized using conventional UHT (ultra high temperature) treatment and pasteurization technology. The pasteurized liquid is then cooled and held refrigerated until ready to dry. All of the water-soluble vitamins, trace minerals, and free amino acids are then added with sufficient water just prior to drying. Product is then brought to a final solids concentration that is adequate for spray drying using conventional technology. Once spray dried, maltodextrin is dry blended into the spray dried product, or alternatively, the maltodextrin can be replaced with equivalent solids from pregelatinized starch.

The spray dried formula is then packaged and sealed in multi-dose containers, from which portions thereof are removed and diluted with water prior to use to form the desired caloric density infant formula (e.g., 20-24 kcal/fl. oz.), and then fed to infants to provide their primary, secondary, or supplemental nutritional needs.

The packaged nutritional powders exhibit improved stability in the form of reduced rancid oil characteristics and reduced vitamin A degradation over prolonged periods of time after storage and prior to initially opening the sealed container, e.g., 6-24 months.

Example 2

This example illustrates a lactose-free nutritional powder of the present invention, including a method of making the formula and a method of using the formula to provide infant nutrition. The formula ingredients for a 3,400 kg batch are listed below in following table.

TABLE 2

Lactose-free Infant Formula Powder

| INGREDIENT | AMOUNT |
| --- | --- |
| High oleic safflower oil | 387 kg |
| Coconut oil | 290 kg |
| Soy oil | 290 kg |
| Ascorbyl palmitate | 2.9 kg |
| Cystine dihydrochloride | 3.8 kg |
| Oil soluble vitamin premix | 1.5 kg |
| Milk protein isolate | 436 kg |
| Calcium phosphate | 35 kg |
| Calcium carbonate | 1 kg |
| Potassium citrate | 28 kg |
| Magnesium chloride | 4.6 kg |
| Potassium chloride | 22.2 kg |
| Sucrose | 372 kg |
| Potassium iodide | 5.1 g |
| Corn syrup | 1,269 kg |
| Ferrous sulfate | 1.54 kg |
| Water soluble vitamin/trace minerals/taurine premix | 5 kg |
| Choline chloride | 1.5 kg |
| Choline bitartrate | 1.6 kg |
| Nucleotides | 2.2 kg |
| L-carnitine | .367 kg |
| Riboflavin | .018 kg |
| Ascorbic acid | 5.4 kg |

To prepare the nutritional powder described above, an aqueous slurry containing the carbohydrate/sucrose and minerals is formed with heat (120°-160° F.) and agitation. An oil blend is then prepared with heat (120°-150° F.) and agitation, which contains the formula oils, antioxidants and oil soluble vitamins. The protein is then added to the oil blend followed by the addition of the aqueous slurry, all with agitation. The pH of the resulting combination is adjusted as needed to reach 6.5-6.9. The combination is then heat-treated and homogenized using conventional HTST (high temperature short time) treatment and pasteurization technology. The pasteurized liquid is then cooled and refrigerated until ready to dry. Just before drying, all of the water-soluble vitamins, trace minerals, and free amino acids are added with sufficient water to the pasteurized liquid, and then the resulting mixture is brought to a final solids concentration that is adequate for spray drying using conventional technology.

The spray dried formula is then packaged and sealed in multi-dose containers, from which portions thereof are removed and diluted with water prior to use to form the desired caloric density infant formula (e.g., 20-24 kcal/fl oz.), and then fed to infants to provide their primary, secondary, or supplemental nutritional needs.

The packaged nutritional powder exhibits improved stability in the form of reduced rancid oil characteristics and reduced vitamin A degradation over prolonged periods of time after storage and prior to initially opening the sealed container, e.g., 6-24 months.

Example 3

This example illustrates a lactose-free nutritional powder of the present invention, including a method of making the formula and a method of using the formula to provide infant nutrition. The formula ingredients for a 3,400 kg batch are listed below in following table.

TABLE 3

Lactose-free Infant Formula Powder

| INGREDIENT | AMOUNT |
| --- | --- |
| High oleic safflower oil | 406 kg |
| Coconut oil | 275 kg |
| Soy oil | 275 kg |
| Ascorbyl palmitate | 1.5 kg |
| Cystine dihydrochloride | 3.6 kg |
| Oil soluble vitamin premix | 1.2 kg |
| Milk protein isolate | 442 kg |
| Calcium phosphate | 20 kg |
| Calcium carbonate | 30 kg |
| Potassium citrate | 13 kg |
| Magnesium chloride | 10.5 kg |
| Potassium chloride | 18.6 kg |
| Sucrose | 360 kg |
| Potassium iodide | 5.1 g |
| Corn syrup | 1,300 kg |
| Ferrous sulfate | 1.54 kg |
| Water soluble vitamin/trace minerals/taurine premix | 5 kg |
| Choline chloride | 1.5 kg |
| Choline bitartrate | 1.6 kg |
| Nucleotides | 2.2 kg |
| L-carnitine | .367 kg |
| Riboflavin | .018 kg |
| Ascorbic acid | 5.4 kg |
| Rice Starch | 170 kg |
| Tuna Oil | 6.8 kg |
| Arachidonic Acid (Fungal Oil) | 9.7 kg |

To prepare the nutritional powder described above, an aqueous slurry containing the sucrose and minerals is formed with heat (120°-160° F.) and agitation. An oil blend is then prepared with heat (120°-150° F.) and agitation, which contains the formula oils, antioxidants and oil soluble vitamins. The protein is then added to the oil blend followed by the addition of the aqueous slurry, corn syrup and starch, all with agitation. The pH of the resulting combination is adjusted as needed to reach 6.5-6.9. The combination is then heat-treated and homogenized using conventional HTST (high temperature short time) treatment and pasteurization technology. The pasteurized liquid is then cooled and refrigerated until ready to dry. Just before drying, all of the water-soluble vitamins, trace minerals, and free amino acids are added with sufficient water to the pasteurized liquid, and then the resulting mixture is brought to a final solids concentration that is adequate for spray drying using conventional technology. Alternatively, the starch may be added just prior to drying or dry blended into a spray-dried base powder. The final powder formula is then packaged and sealed in multi-dose containers, from which portions thereof are removed and diluted with water prior to use to form the desired caloric density infant formula (e.g., 20-24 kcal/fl oz.), and then fed to infants to provide their primary, secondary, or supplemental nutritional needs.

The packaged nutritional powder exhibits improved stability in the form of reduced rancid oil characteristics and reduced vitamin A degradation over prolonged periods of time after storage and prior to initially opening the sealed container, e.g., 6-24 months.

Experiment

Two separate studies were performed to evaluate the nutritional powders of the present invention for oxidative stability. In the first study, the powders were evaluated for oxidative stability as measured by a sensory model described hereinafter. In a second study, the powders were evaluated by the sensory model and were also evaluated for vitamin A reduction/degradation over defined periods of time.

The nutritional powder samples formulated for and evaluated in Study I were similar to commercially available SIMILAC® Lactose Free Infant Formula (Ross Products Division, Abbott Laboratories, Columbus, Ohio, USA) except that the sample powders were modified to include different antioxidant systems. The base formula used to prepare each test sample contained (per 100 kcal): protein 2.14 gm (milk protein isolate), fat 5.4 gm (high-oleic safflower, soy, coconut oils, arachidonic acid, docosahexaenoic acid), carbohydrate 10.7 gm (corn syrup, rice starch, sucrose), minerals (calcium 85 mg, phosphorus 56 mg, magnesium 6 mg, sodium 30 mg, potassium 107 mg, chloride 65 mg, iron 1.6 mg, zinc 0.75 mg, copper 0.09 mg, iodine 0.009 mg, manganese 5 µg) and vitamins (vitamin A 300 IU, vitamin D 60 IU, vitamin E 3 IU, vitamin $K_1$ 8 µg, vitamin C 12 mg, thiamin 0.100 mg, riboflavin 0.150 mg, pyridoxine 0.060 mg, niacin 1050 mg, vitamin $B_{12}$ 0.25 µg, folic acid 15 µg, pantothenic acid 0.450 mg, biotin 4.4 µg, choline 16 mg, inositol 4.3 mg) and selenium 1.8 µg. The control was the base formula without additional ingredients, and the test samples were the base formula with specific anti oxidant systems added. The tested samples and control are described in Table 5 along with the study results.

The nutritional powder samples formulated for and evaluated in Study II were similar to commercially available SIMILAC® Lactose Free Infant Formula (Ross Products Division, Abbott Laboratories, Columbus, Ohio, USA) except that the sample powders were modified to include different antioxidant systems. The base formula used to prepare each test sample contained (per 100 kcal): protein 2.14 gm (milk protein isolate), fat 5.4 gm (high-oleic safflower, soy, coconut oils), carbohydrate 10.7 gm (corn syrup, sucrose), minerals (calcium 85 mg, phosphorus 56 mg, magnesium 6 mg, sodium 30 mg, potassium 107 mg, chloride 65 mg, iron 1.6 mg, zinc 0.75 mg, copper 0.09 mg, iodine 0.009 mg, manganese 5 µg) and vitamins (vitamin A 300 IU, vitamin D 60 IU, vitamin E 3 IU, vitamin $K_1$ 8 µg, vitamin C 12 mg, thiamin 0.100 mg, riboflavin 0.150 mg, pyridoxine 0.060 mg, niacin 1050 mg, vitamin $B_{12}$ 0.25 µg, folic acid 15 µg, pantothenic acid 0.450 mg, biotin 4.4 µg, choline 16 mg, inositol 4.3 mg) and selenium 1.8 µg. The control was the base formula without additional ingredients, and the test samples were the base formula with specific anti oxidant systems added. The tested samples and control are described in Table 6 along with the study results.

Preparation

Each sample formula was batched, processed, and spray dried in a pilot plant facility. As noted above, each sample formula was based upon commercial Similac™ Lactose Free Infant Formula powder with adjustments to the antioxidant system. The batching scheme involved making an initial common oil blend without an antioxidant system. The common oil blend was split into portions, and designated antioxidants were added to each portion to make up distinct variables. Protein was added to the oil, and then the resulting protein and fat slurry was combined with an aqueous slurry containing carbohydrate/corn syrup and minerals. The resulting blend was HTST (high temperature short time) processed and homogenized at about 45% solids. The blends were standardized with vitamins, trace minerals and citrate (when required), then UHT (ultra high temperature) processed before feeding to the spray dryer at about 45% solids. The powders were dried to a moisture content of about 2-3% by weight of the powder.

The spray dried powders were packaged in cans with a 0.5 inch (1.27 cm) headspace, with fill weights ranging from 370 to 390 grams, and flushed with nitrogen to less than 2% oxygen headspace, and sealed with a sanitary seamer.

Evaluation

An open can evaluation was conducted in each study. The formulated samples were pulled at 0, 2, and 4 week intervals. Oxygen headspace was tested prior to opening the actual can used in each evaluation. The zero interval represents the time when the can was originally opened. Between sampling, the cans were sealed with plastic commercial can overcaps. Sample powders in both studies were subjected to sensory oxidation method (e.g., sensory evaluation or detection of rancid flavor and/or aroma) at 0, 2, and 4 weeks. Sample powders in the second study were evaluated for vitamin A levels at 0 and 4 weeks.

The sensory evaluation method provides an indirect evaluation of oxidative stability by sensory detection of rancid flavor and/or odor intensity. To perform the sensory evaluation method, trained descriptive panelists were recruited (e.g., certified by Arthur D. Little Company). Oxidation panels were run which consisted of 2 or more panelists. Data were generated by consensus. Samples were reconstituted prior to evaluation and served at room temperature. Panelists evaluated each sample for degree of oxidation in accordance with the 5-point scale described below in Table 4.

TABLE 4

Sensory Oxidation Evaluation Method

| Scale | Oxidation | Sensory |
|---|---|---|
| 0 | None | No oxidized flavor notes detected |
| 1 | very slight | Product has threshold to very slight intensity of oxidized flavor notes |
| 2 | slight | Product has slight oxidized flavor notes |
| 3 | moderate | Product has moderate to above intensity of oxidized flavor notes, but no "painty" notes detected |
| 4 | much (rancid) | Product has threshold or above intensity of "painty" notes; may also have oxidized flavor notes at any intensity |
| 5 | extreme (rancid) | Product has a moderate or above intensity of "painty" notes. It may also have oxidized flavor notes at any intensity. |

Powder samples from the second study were also evaluated for vitamin A concentrations and reductions thereof over time. Samples that were pulled for vitamin A analysis were either tested the same day or held frozen until testing. Samples submitted for vitamin A analysis were wrapped in aluminum foil to reduce exposure to light that might lead to loss of vitamin activity.

Oxidative Stability Results

The results from the sensory oxidation evaluation (Studies I and II) and the vitamin A measurements (Study II) are referenced below in Tables 5 and 6.

TABLE 5

Oxidative Stability Results (Study I)

| | Anti-oxidant System* ppm by weight of powder | | | | Sensory oxidation Scores Scale 0-5 scale at 0, 2, 4 wks after package initially opened 0 = no rancid odor detected 5 = extreme rancid odor detected | | |
|---|---|---|---|---|---|---|---|
| Sample | Cys | AP | Toco | Cit | 0 weeks | 2 weeks | 4 weeks |
| 1 | — | 350 | 120 | 2000 | 4 | 5 | 5 |
| 2 | — | 500 | 120 | 2000 | 5 | 5 | 5 |
| 3 | 850 | 350 | 120 | 2000 | 4 | 5 | 5 |
| 4 | 850 | 500 | 120 | 2000 | 0 | 0 | 0 |

*Cystine (Cys); AP (ascorbyl palmitate); Toco (tocopherol); Cit (potassium citrate)

TABLE 6

Oxidative Stability Results (Study II)

| | Anti-oxidant System* ppm by weight of powder | | | | Sensory oxidation Scores Scale 0-5 scale at 0, 2, 4 wks after package initially opened 0 = no rancid odor detected 5 = extreme rancid odor detected | | | Vitamin A Stability measured vitamin A level (IU/kg) at 0 and 4 wks after package initially opened | |
|---|---|---|---|---|---|---|---|---|---|
| Sample | Cys | AP | Toco | Cit | 0 weeks | 2 weeks | 4 weeks | 0 weeks | 4 weeks |
| 1 | — | — | — | — | 4 | 4 | 5 | 19710 | 11030 |
| 2 | 1700 | — | — | — | 0 | 4 | 4 | 27100 | 24600 |
| 3 | — | 900 | — | — | 0 | 4 | 4 | 28900 | 30200 |
| 4 | 850 | 900 | — | 4000 | 0 | 0 | 0 | 31107 | 30115 |
| 5 | 1700 | 900 | — | — | 0 | 0 | 0 | 32603 | 31801 |
| 6 | — | — | 300 | — | 3 | 4 | 5 | 22060 | 19780 |
| 7 | — | — | — | 4000 | 4 | 4 | 5 | 21960 | 17000 |

TABLE 6-continued

Oxidative Stability Results (Study II)

| | Anti-oxidant System* ppm by weight of powder | | | | Sensory oxidation Scores Scale 0-5 scale at 0, 2, 4 wks after package initially opened 0 = no rancid odor detected 5 = extreme rancid odor detected | | | Vitamin A Stability measured vitamin A level (IU/kg) at 0 and 4 wks after package initially opened | |
|---|---|---|---|---|---|---|---|---|---|
| Sample | Cys | AP | Toco | Cit | 0 weeks | 2 weeks | 4 weeks | 0 weeks | 4 weeks |
| 8 | 1700 | 900 | 150 | 2000 | 0 | 0 | 0 | 24600 | 27700 |
| 9 | 1700 | 900 | 300 | 4000 | 0 | 0 | 0 | 32400 | 34500 |
| 10 | 850 | — | 150 | 4000 | 1 | 5 | 4 | 24300 | 24900 |
| 11 | 1700 | — | 300 | 4000 | 0 | 5 | 5/0 | 30000 | 29000 |
| 12 | 1700 | — | 150 | 4000 | 0 | 0 | 0 | 31000 | 30700 |
| 13 | — | 900 | 150 | 4000 | 0 | 0 | 0 | 32100 | 31800 |
| 14 | — | 900 | 300 | — | 0 | 0 | 0 | 28600 | 32000 |
| 15 | 1700 | 900 | 150 | — | 0 | 0 | 0 | 31800 | 31800 |

*Cystine (Cys); AP (ascorbyl palmitate); Toco (tocopherol); Cit (potassium citrate)

Summary

The collective data from the studies show that antioxidant systems containing selectively high ascorbyl palmitate concentrations are highly effective in providing oxidative stability to the base powder formula tested. Although ascorbyl palmitate is a known anti-oxidant for oil-containing systems, and the above-described formulas are in fact oil-containing compositions, it is also known that ascorbyl palmitate alone is not a particularly effective stability agent, and is therefore often used in combination with other antioxidants. The data was especially surprising because, not only was ascorbyl palmitate effective when used alone in delaying oxidation and providing Vitamin A stability, it was effective when used alone in an otherwise highly oxidatively unstable powder such as the base formula described above. Moreover, oxidative stability was also shown even in the 4 week open can test with minimal amounts of other anti-oxidants, provided that the powder contained high ascorbyl palmitate concentrations.

The data as shown in the previous table were also surprising in that any combination of cystine and ascorbyl palmitate was found to be a highly effective antioxidant system when used in the oxidatively unstable base formula to which the experiments were directed. This combination has not heretofore been described as an effective anti oxidation or stability system.

What is claimed is:

1. A nutritional powder comprising
   (a) carbohydrate,
   (b) lipid,
   (c) protein,
   (d) from about 500 to about 1000 ppm of ascorbyl palmitate, and
   (e) from about 800 to about 2000 ppm of at least one free amino acid selected from the group consisting of cystine, cysteine, or combinations thereof,
   wherein the nutritional powder includes less than 25% lactose as a percentage of total carbohydrate calories.

2. The nutritional powder of claim 1, wherein the powder comprises less than 200 ppm of lactose.

3. The nutritional powder of claim 1, wherein the powder comprises from about 600 ppm to about 800 ppm ascorbyl palmitate by weight of the nutritional powder.

4. The nutritional powder of claim 1, wherein the powder comprises from about 800 ppm to about 1200 ppm by weight of at least one free amino acid selected from the group consisting of cystine, cysteine, or combinations thereof.

5. The nutritional powder of claim 1, wherein the powder comprises from about 1% to about 50% unsaturated lipid as a percentage of total lipid calories in the powder.

6. A nutritional powder comprising
   (a) carbohydrate,
   (b) lipid,
   (c) protein,
   (d) from about 500 to about 1000 ppm of ascorbyl palmitate, and
   (e) from about 800 to about 2000 ppm of at least one free amino acid selected from the group consisting of cystine, cysteine, or combinations thereof.

7. The nutritional powder of claim 6, wherein the powder comprises from about 600 ppm to about 800 ppm ascorbyl palmitate by weight of the powder.

8. The nutritional powder of claim 6, wherein the powder comprises from about 800 ppm to about 1200 ppm of at least one free amino acid selected from the group consisting of cystine, cysteine, or combinations thereof.

9. A method of providing nutrition to an infant, said method comprises reconstituting the composition of claim 1 with water to a caloric density of at least about 660 kcal/liter, and feeding said infant the reconstituted composition.

10. A method of providing nutrition to an infant, said method comprises reconstituting the composition of claim 6 with water to a caloric density of at least about 660 kcal/liter, and feeding said infant with the reconstituted composition.

* * * * *